United States Patent [19]

Thompson

[11] 4,354,025

[45] Oct. 12, 1982

[54] N,N'-DISUBSTITUTED HEXAHYDROPYRIMIDINES

[75] Inventor: Neil E. S. Thompson, Creve Coeur, Mo.

[73] Assignee: Petrolite Corporation, St. Louis, Mo.

[21] Appl. No.: 916,390

[22] Filed: Jun. 16, 1978

Related U.S. Application Data

[62] Division of Ser. No. 815,886, Jul. 15, 1977, Pat. No. 4,129,597.

[51] Int. Cl.$^3$ .................. C07D 235/02; C07D 235/06
[52] U.S. Cl. ............................. 544/231; 260/814
[58] Field of Search ........................................ 544/231

[56] References Cited

U.S. PATENT DOCUMENTS

| | | | |
|---|---|---|---|
| 2,486,648 | 11/1949 | Haury | 544/242 |
| 2,525,855 | 10/1950 | Bergmann | 544/231 |
| 3,248,243 | 4/1966 | Hodge et al. | 106/125 |
| 4,085,105 | 4/1978 | Alink | 544/231 |

FOREIGN PATENT DOCUMENTS 559890 3/1944 United Kingdom ................ 544/231

OTHER PUBLICATIONS

Amarego et al., Chem. Abstracts, 71 (1969), 69950t.

*Primary Examiner*—Paul M. Coughlan, Jr.
*Attorney, Agent, or Firm*—Sidney B. Ring; Hyman F. Glass

[57] ABSTRACT

This invention relates to hexahydropyrimidines prepared by condensing cyclohexanone, or derivatives thereof, with ammonia to yield tetrahydropyrimidines, which can be reduced to hexahydropyrimidines, whose pyrimidine ring can be broken to yield diamines having one primary amino group, which primary group can be reacted with a carbonyl to yield Schiff base imines, which Schiff base imines can be reduced to N-substituted amino groups. The two amino groups of the reduced Schiff base can be bridged by reaction with an aldehyde to form the novel N,N'-disubstituted hexahydropyrimidines.

This invention also relates to the use of these products as antioxidants.

4 Claims, No Drawings

N,N'-DISUBSTITUTED HEXAHYDROPYRIMIDINES

This is a Division of Application Ser. No. 815,886, filed July 15, 1977, by Neil E. S. Thompson, now U.S. Pat. No. 4,129,597 for Amino Compounds and Use Thereof as Antioxidants.

In Ser. No. 292,494 filed on Sept. 27, 1972, now U.S. Pat. No. 4,085,104, there is described and claimed substituted 2, 3, 4, 5-tetrahydropyrimidines (THP)

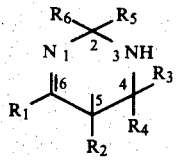

Formula I which are prepared by the following reactions:
(1) The reaction of a carbonyl compound (ketone or aldehyde) with ($NH_3$ or $NH_4OH$) and a sulfur-containing catalyst.
(2) The reaction of an α, β-unsaturated ketone and a carbonyl compound and $NH_3$ (or $NH_4OH$) without a catalyst.
(3) Reaction of an α, β-unsaturated ketone, a 1-amino-alcohol and $NH_3$ (or $NH_4OH$) without a catalyst.

In the above formula, $R_1$, $R_2$, $R_3$, $R_4$, $R_5$ and $R_6$, which may be the same or different, are hydrogen or substituted group such as alkyl, aryl, cycloalkyl, alkaryl, aralkyl, heterocyclic, substituted derivatives thereof, etc. In addition R groups may be joined in a cyclic configuration which makes the THP structure a part of the substituted group.

Alkyl includes methyl, ethyl, propyl, butyl, amyl, hexyl, heptyl, octyl, nonyl, decyl, undecyl, dodecyl, tridecyl, tetradecyl, pentadecyl, hexadecyl, heptadecyl, octadecyl, escosyl, docosyl, etc. for example having about 1-25 or more carbons such as from about 1-18 carbons, but preferably about 1-12 carbons. The term "alkyl" also includes isomers of the straight chain where branching occurs.

Cycloalkyl includes cyclopentyl, cyclohexyl, etc. and derivatives thereof such as alkyl-cyclohexyl, dialkylcyclohexyl, etc.

Aryl, alkaryl and aralkyl, including phenyl, alkylphenyl, polyalkylphenyl, chlorophenyl, alkoxyphenyl, naphthyl, alkylnapththyl, etc., benzyl, substituted benzyl, etc.

The joining of the R groups into a ring structure include those structures derived from reactants of the general formula

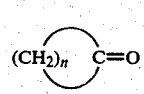

such as cyclohexanone, cyclopentanone, substituted derivatives thereof such as alkyl-cyclohexanone, dialkyl-cyclohexanone.

Ser. No. 597,564, now abandoned discloses that 2,2-disubstituted derivatives of Formula I can be converted to linear diamines such as N-substituted-2,4-diamino-2-substituted pentanes by hydrogenation.

It was further disclosed in Ser. No. 597,564 that such reaction occurs only with the 2,2-di-substituted tetrahydropyrimidines. Where the 2,2-di-substitution is not present, the corresponding cyclic hexahydropyrimidines are formed instead of the linear diamines.

Ser. No. 597,564 also disclosed further that a compound of Formula II can be converted to an amine-imine by reacting with a carbonyl compound.

Ser. No. 597,564 also disclosed the amine-imine can be converted to the corresponding N,N'-substituted diamines by hydrogenation.

These reactions may be summarized as follows:

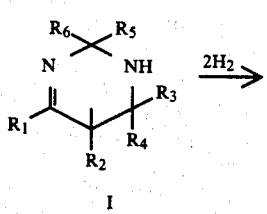

I

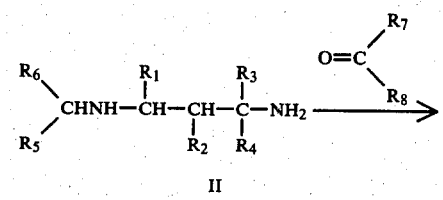

II

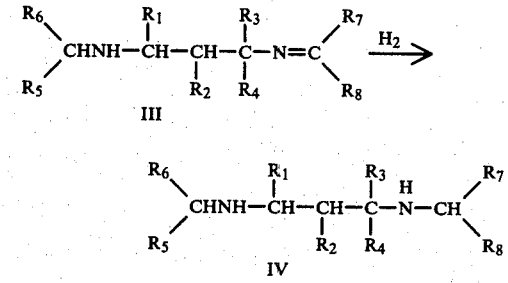

III

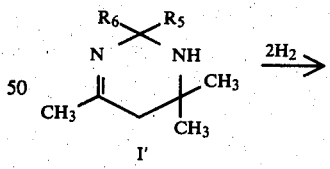

IV or more specifically as follows:

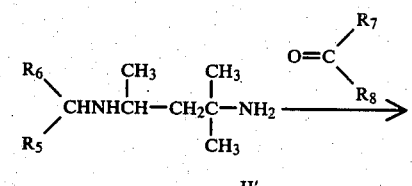

I'

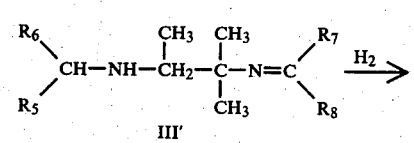

II'

III'

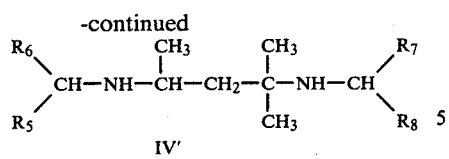
IV'

Although the above reactions are illustrated with the trimethyl tetrahydropyrimidine, the methyl groups may be replaced with other groups such as for example hydrogen, higher alkyls, aryls, cycloalkyls, etc.

The hydrogenation reaction is carried out in the presence of a hydrogenation catalyst such as palladium, platinum, nickel, etc.; at a suitable temperature, for example from ambient to 200° C. or higher, but preferably 50°-150° C.; at pressures sufficient to contain hydrogen in the reaction vessel, such as about 10-2000 psi, or higher but preferably about 200-1000 psi; for a sufficient period of time for the reaction to take place such as from about 10 minutes to 24 hrs. or longer, preferably from about ½ hr. to 6 hrs.; in solvents which do not interfere with the catalyst, reactants, or products such as water, alcohol, hydrocarbons, esters, etc.

In addition, reduction can be effected with compositions which on reaction yield hydrogen such as metal hydrides, etc.

The linear amine resulting from hydrogenation is then reacted with a carbonyl compound of the formula

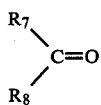

which is either an aldehyde or a ketone.

The preparation of the imine compound is conventional. For example the reaction can be carried out by heating the amine with substantially stoichiometric amounts of the carbonyl compound under dehydrating conditions, i.e., 1:1 molar ratio, for example by the use of an azeotroping agent.

The imine compound resulting from the carbonyl reaction can be further reduced in the manner of Step 1 to yield the substituted diamine.

In the above formula, $R_7$ and $R_8$, which may be the same or different, are hydrogen or substituted group such as alkyl, aryl, cycloalkyl, alkaryl, aralkyl, heterocyclic, substituted derivatives thereof, etc. In addition R groups may be joined in a cyclic configuration.

Alkyl includes methyl, ethyl, propyl, butyl, amyl, hexyl, heptyl, octyl, nonyl, decyl, undecyl, dodecyl, tridecyl, tetradecyl, pentadecyl, hexadecyl, heptadecyl, octadecyl, escosyl, docosyl, etc., for example having about 1-25 or more carbons such as from about 1-18 carbons, but preferably about 1-12 carbons. The term "alkyl" also includes isomers of the straight chain where branching occurs.

Cycloalkyl includes cyclopentyl, cyclohexyl, etc. and derivatives thereof such as alkyl-cyclohexyl, dialkylcyclohexyl, etc.

Aryl, alkaryl and aralkyl include phenyl, alkylphenyl, polyalkylphenyl chlorophenyl, alkoxyphenyl, naphthyl, alkylnaphthyl, etc., benzyl, substituted benzyl, etc.

The joining of the R groups into a ring structure include those structures derived from reactants of the general formula

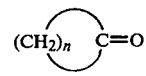

such as cyclohexanone, cyclopentanone, substituted derivatives thereof such as alkyl-cyclohexanone, dialkyl-cyclohexanone.

The following examples are presented for purposes of illustration and not of limitation.

EXAMPLE 1

N-Cyclohexyl-2,4-diamino-2-methylpentane

In a 1 liter stirred autoclave was placed 95 g of 2,2-pentamethylene-4,4,6-trimethyl-2,3,4,5-tetrahydropyrimidine, 200 cc. of methanol and 6 g of 5% Pt/C catalyst. The autoclave was pressurized with 400 psi of hydrogen gas and the mixture heated for 75 minutes at 75°-80° C. while a pressure of 400-800 psi was maintained. The reaction product was removed through an internal filter leaving the catalyst behind. After removal of the solvent, there was isolated 95 g of N-cyclohexyl 2,4-diamino-2-methylpentane.

The analytical data were consistent with the assigned structure

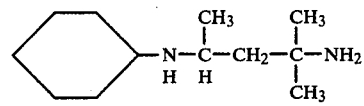

Anal. calced for $C_{12}H_{26}N_2$; N, 14.14; Found; N, 13.98.

EXAMPLE 2

N-Cyclohexyl, N'-isobutyl 2,4-diamino-2-methylpentane

A sample of 50 g of N-cyclohexyl-2,4-diamino-2-methylpentane and 18.7 g of isobutyraldehyde in 50 cc of benzene was refluxed under azeotropical conditions for 1 hr. The benzene was removed under diminished pressure to yield 67 g of product. The product was dissolved in 200 cc of methanol and 9.6 g of sodium boronhydride was slowly added with stirring. After the reaction was completed, the solvent was removed under diminished pressure. To the resulting product was added water and the organic layer was separated. The aqueous layer was extracted with ether and the ethereal solution combined with the organic layer. After removal of the ether under diminished pressure the product was distilled under diminished pressure to yield 60 g of N-Cyclohexyl, N'-isobutyl 2,4-diamino-2-methylpentane, $b_{0.6}=98°$ C.

Anal. calcd. for $C_{16}H_{32}N_2$; N, 11.11; Found; N, 11.01.

The analytical data were consistent with the assigned structure

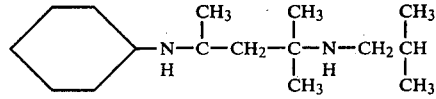

EXAMPLE 3

N-Cyclohexyl, N' isobutyl 2,4-diamino-2-methylpentane and 18.7 g of isobutyraldehyde in 50 cc of benzene was refluxed under azeotropical conditions for 1 hour. After removal of the solvent, the product was dissolved in 100 cc of methanol and placed with 2 g of a 10% Pt/C catalyst in an autoclave. The reaction was pressurized with 400 psi of hydrogen and the mixture was heated with stirring for 3 hrs. at 75°–80° C. After removal of the catalyst by filtration, the methanol was removed under diminished pressure to yield 67 g of N-Cyclohexyl, N'-isobutyl 2,4-diamino-2-methylpentane, identical in all respects to the product isolated as described in example 2.

EXAMPLE 4

N-Cyclohexyl, N'-isobutyl 2,4-diamino-2-methylpentane

In a 1 liter stirred autoclave was placed 95 g of 2,2-pentamethylene 4,4,6-trimethyl 2,3,4,5-tetrahydropyrimidine, 200 cc of methanol and 6 g of 5% Pt/C catalyst. The mixture was hydrogenated with stirring for 60 minutes at 75°–80° C. and 400–800 psi of hydrogen. To the mixture was added 39 g of isobutyraldehyde and hydrogenation was continued for 3 hrs. at 75°–80° C. and 400–800 psi of hydrogen pressure. The catalyst was removed and the mixture evaporated under diminished pressure, to yield 116 g of N-cyclohexyl, N'-isobutyl 2,4-diamino-2-methylpentane, identical in all respects to the product isolated as described in example 2.

The following 2,4-diamino-2-methylpentanes were prepared, according to the methods described in examples 1–4. The results are summarized in Table I.

TABLE I

General Structure:

$$R_1-\underset{H}{\underset{|}{C}}-\underset{H}{\underset{|}{N}}-\underset{H}{\overset{CH_3}{\underset{|}{C}}}-\underset{H}{\underset{|}{C}}-\underset{CH_3}{\overset{CH_3}{\underset{|}{C}}}-\underset{H}{\underset{|}{N}}-\underset{H}{\underset{|}{C}}-R_4$$

| Ex. No. | $R_1$ | $R_2$ | $R_3$ | $R_4$ |
|---|---|---|---|---|
| 5 | $CH_3$ | $CH_3$ | — | —* |
| 6 | $CH_3$ | $CH_3$ | H | $CH(CH_3)_2$ |
| 7 | $CH_3$ | $CH_3$ | H | $CH_2-CH_2-CH_3$ |
| 8 | $CH_3$ | $CH_3$ | H | Phenyl |
| 9 | $CH_3$ | $CH_3$ | $-CH_2-CH_2-CH(CH_3)-CH_2-CH_2-$ | |
| 10 | $CH_3$ | $C_2H_5$ | — | —* |
| 11 | $CH_3$ | $C_2H_5$ | H | $CH(CH_3)_2$ |
| 12 | $-(CH_2)_5-$ | | H | $C_2H_5$ |
| 13 | $-(CH_2)_5-$ | | H | $CH_2-CH_2-CH_3$ |
| 14 | $-(CH_2)_5-$ | | $-(CH_2)_5-$ | |
| 15 | $-(CH_2)_5-$ | | H | Phenyl |
| 16 | $-(CH_2)_5-$ | | H | $CH(C_2H_5)_2$ |
| 17 | $-(CH_2)_5-$ | | H | $CH_3$ |
| 18 | $-(CH_2)_5-$ | | $-CH_2-CH(CH_3)-CH_2-CH_2-CH_2-$ | |
| 19 | $-(CH_2)_5-$ | | $-CH_2-CH_2-CH(CH_3)-CH_2-CH_2-$ | |

*where $\underset{H}{\underset{|}{C}}-R_4 = H$

The novel compounds of this invention are analogous to those of the general formulas of Ser. No. 597,564. Thus, the formulas of Ser. No. 597,564 are modified as follows:

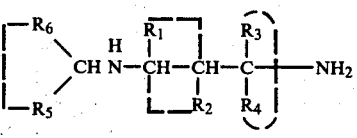

so that the dotted lines indicate cyclic structures as follows:

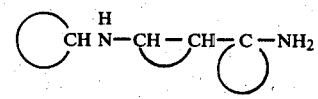

In the case of

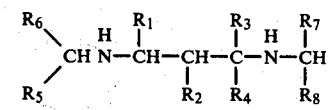

the modification is as follows:

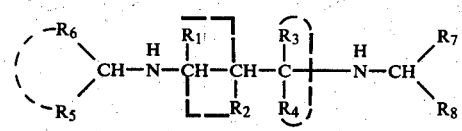

to yield:

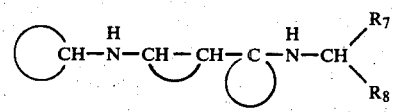

The two amino groups can be bridged by reaction with an aldehyde such as formaldehyde so that the above formula becomes

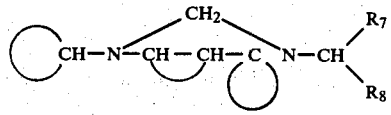

In the above formulae, ◯ indicates the moiety of a cycloalkyl group or a substituted cycloalkyl group for example substituted with an alkyl, halo, alkoxyl, phenyl, etc. group. The preferred cycloalkyl group is cyclohexyl.

Compounds analogous to those described in Ser. No. 597,564 have been prepared. These are summarized by the following.

1. Cyclohexanone condensed with ammonia to yield tetrahydropyrimide as follows:

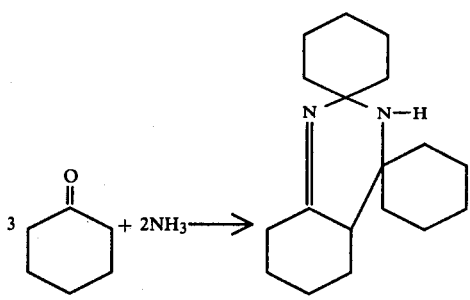

2. Reduction of tetrahydropyrimidines to hexahydropyrimines as follows:

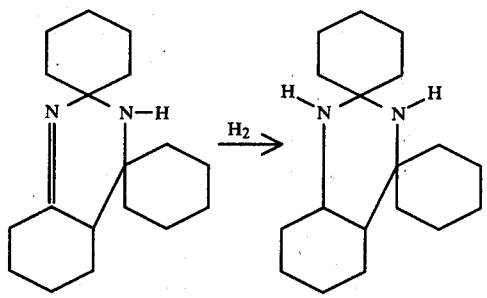

3. Reductive scission of hexahydropyrimidines to form linear diamines as follows:

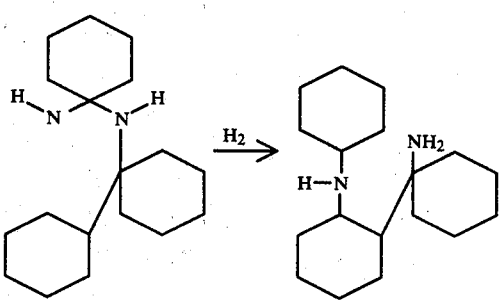

4. Reductive alkylation by formation of the Schiff base imine and reduction thereof as follows:

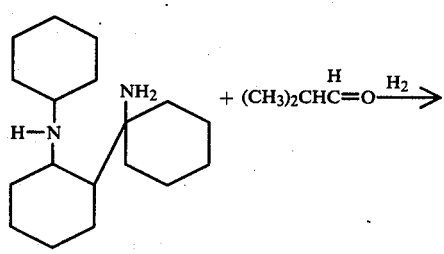

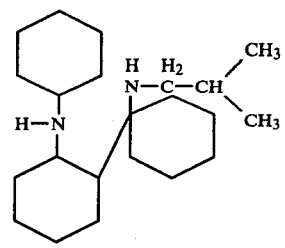

5. Formation of Hexahydropyrimides by bridging the two amino groups with an aldehyde as follows:

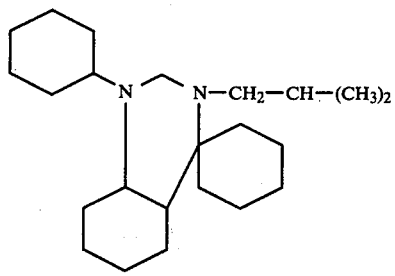

The following examples are presented for purposes of illustration and not of limitation.

EXAMPLE 1A 2,2,4,4-Dipentamethylene 5,6-tetramethylene 2,3,4,5-tetrahydropyrimidine To a mixture of 294 grams of cyclohexanone and 5 grams of ammonium chloride placed in a pressure reactor was added over a ¾ hour period 38.8 grams of ammonia gas. After the addition was completed, the mixture was stirred for 5 hours at ambient temperature. The product was taken up in toluene and the aqueous phase which separated was discarded. The toluene solution was evaporated under diminished pressure to yield 268 grams of 2,2,4,4-dipentamethylene-5,6-tetramethylene-2,3,4,5-tetrahydropyrimidine; infrared spectrum, 6.02μ (C=N); $C^{13}$ n.m.r. spectrum: solvent $CDCl_3$, reference T.M.S.:

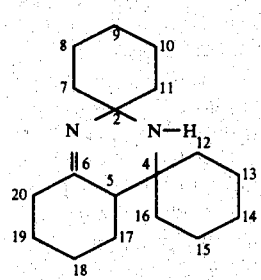

70.11 (2); 50.16 (4); 46.59 (5);
169.38 (6); 38.53 (7); 22.55 (8);
26.38 (9); 22.55 (10); 38.53 (11);
40.61 (12); 21.90 (13); 26.38 (14);
21.64 (15); 35.54 (16); 29.30 (17);
26.38 (18); 29.30 (19); 42.43 (20)

EXAMPLE 2A 2-(1'-aminocyclohexyl)-Dicyclohexylamine

A sample of 30 grams of the product described in example 1A, 300 cc. of methanol and 2 grams of a 5% Pt/C catalyst were placed in a 1 l. autoclave. To the mixture was added 800 psi of hydrogen gas and the mixture was heated with stirring for 2½ hours at 75°–80° C. After removal of the catalyst by filtration and the solvent by evaporation there was isolated 29 grams of 2-(1'-aminocyclohexyl)dicyclohexylamine: $C^{13}$ n.m.r. spectrum

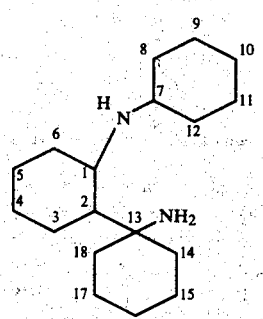

49.31 (1); 47.97 (2); 29.38 (3);
24.84 (4); 22.20 (5); 33.24 (6);
53.12 (7); 35.75 (8); 26.26 (9);
26.91 (10); 26.26 (11); 35.75 (12);
52.84 (13); 37.46 (14); 20.41 (15);
25.28 (16); 20.09 (17); 38.11 (18).

EXAMPLE 3A 2,2,4,4 Dipentamethylene-5,6-tetramethylene hexahydropyrimidine

A mixture of 294 grams of cyclohexanone and 51 grams of 90% formic acid was placed in a pressure reactor. To the mixture was added with cooling and stirring 58.6 grams of ammonia gas over a ½ hour period. The mixture was stirred for 18 hours at ambient temperature. The resulting product was subjected to a vacuum (25 mm Hg) at 60° C. and the distillate 18 grams of unreacted cyclohexanone and water was discarded. The product was further heated for 3 hours at 120°–125° C. The resulting product 237.6 grams (86%) was identified as 2,2,4,4,-dipentamethylene-5,6-tetramethylene hexahydropyrimidine. $b_{0.5}$ 153°–155° C.

Anal. Cal.ed for $C_{18}H_{32}N_2$; C, 78.20; H, 11.67; N, 10.14. Found; C, 77.94; H, 11.74; N, 10.08.

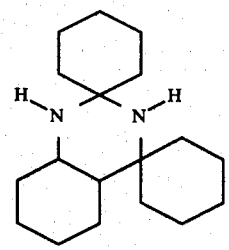

EXAMPLE 4A 2-(1'-aminocyclohexyl)-Dicyclohexylamine

A sample of 30 grams of the product described in example 3A, 300 cc of methanol and 2 grams of a 5% Pt/C catalyst was placed in an autoclave. The mixture was hydrogenated for 3 hours at 800–1000 psi of hydrogen. After removal of the catalyst and solvent, there was isolated 30 grams of 2-(1'-aminocyclohexyl)-dicyclohexylamine, identical in all respects to the product described in Example 2A.

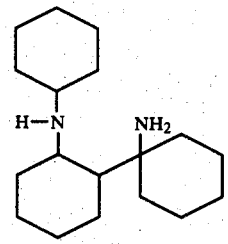

EXAMPLE 5A

N-Cyclohexyl N'-isobutyl 1,2-tetramethylene 3,3-pentamethylene 1,3-diaminopropane A sample of 28 grams of the product described in Example 2A, 7.5 grams of isobutyraldehyde and 300 cc of methanol was placed in a 1 l. autoclave. To the mixture was added 2 grams of a 5% Pt/C catalyst and the mixture was hydrogenated for 1½ hours at 600–800 psi of hydrogen. After removal of the catalyst and solvent, there was isolated 33 grams of a product with spectral characteristics in agreement with the structure shown:

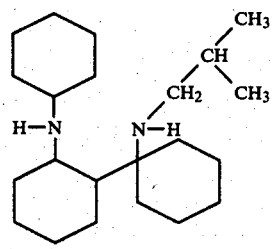

EXAMPLE 6A

1-Cyclohexyl 3-isobutyl 4,4-pentamethylene 5,6-tetramethylene hexahydropyrimidine A mixture of 17 grams of the product described in Example 5A, 1.5 grams of paraformaldehyde and 100 grams of toluene were refluxed under azeotropical conditions for 18 hours. After removal of the toluene under diminished pressure, there was isolated 18 grams of a product with spectral characteristics in agreement with the structure shown:

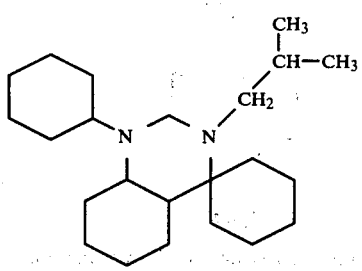

I have discovered that the compositions of this invention preserve and protect organic material subject to deterioration due to oxidation and other influences. They are particularly effective in rubber goods where they function as antioxidants. Accordingly, this invention comprises methods and compositions involving the use of such compositions as antioxidants for the preservation of organic substances which tend to deteriorate in the presence of oxygen including such materials as fish oil, linseed oil, tung oil, carotene, lubricating oils, animal fats, soaps and, especially, rubbery unsaturated organic polymeric materials.

The term "rubbery unsaturated organic polymeric material" is employed to include all natural and synthetic unsaturated rubbery polymeric materials and especially those which may be considered to be polymers of conjugated dienes. Examples of such rubbery materials include the various natural crude rubbers (which are regarded as naturally-occurring isoprene polymers) and such synthetic rubber as polymers of conjugated dienes such as butadiene-1,3, isoprene, 2-methyl butadiene-1,3 and other butadiene-1,3 hydrocarbons, chloroprene, cyano butadiene-1,3 etc., as well as copolymers of these conjugated dienes with each other or with other unsaturated compounds copolymerizable, therewith such as styrene, chlorostyrenes, isobutylene, acrylonitrile, methacrylonitrile, acrylic and methacrylic acids, alkyl acrylates and methacrylates, vinylidene chloride, vinyl pyridine, etc.

These compositions, as antioxidants, are incorporated, in any desired manner, with the oxidizable material to be protected. In general, about 0.25 to 10% of weight of antioxidant based on total weight of material is generally sufficient to obtain adequate protection from oxidation, such as about 0.25 to 5%, for example, from about 0.5 to 4%, but preferably from about 1 to 3%.

The effectiveness of the compounds of the invention as antioxidants is demonstrated by subjecting rubber samples containing them to accelerated heat aging (Test Tube Method) and comparing the relative deterioration of the samples compared to the deterioration shown in similar samples containing no antioxidant (blank) and samples containing three commercially available antioxidants. The three commercial antioxidants are identified as:

a. Agerite Stalite S—a general purpose antioxidant recommended for all elastomers
b. Agerite Superlite—the preferred antioxidant for non-staining and non-discoloring rubber compounding
c. Agerite Resin D—extensively used antioxidant to protect natural and synthetic rubbers against heat and oxidation under most severe service conditions.

The polymer in which these tests were conducted was a natural rubber stock which was formulated and cured as sheets in a conventional manner. The natural rubber composition was prepared in accordance with the following recipe:

| Components | Parts by Weight |
| --- | --- |
| Smoked Sheet | 100.00 |
| Stearic Acid | 2.00 |
| Zinc Oxide | 5.00 |
| Titanium Oxide | 50.00 |
| Altax | 1.00 |
| Methyl Tuads | 0.10 |
| Sulfur | 2.75 |

1.5 part by weight of the selected antioxidant was added to the above mixture to provide a batch. A series of samples containing the selected antioxidant was prepared from the batch. A second series of samples was also prepared which contained no antioxidant, to serve as blanks. All the samples were first cured, their tensile properties determined (ASTM D412), and then they were subjected to accelerated heat aging (T.T. Method) at 212° F. for 96 hours (ASTM D865). Their tensile properties after the heat aging treatment was measured. The results are shown in the following table.

| | Test Data | | | | | |
| --- | --- | --- | --- | --- | --- | --- |
| | Blank | Agerite Stalite S | Agerite Superlite | Agerite Resin D | Example 5A | Example 6A |
| A. Unaged Physicals: ASTM D412 | | | | | | |
| Elongation, % | 570 | 670 | 610 | 650 | 530 | 530 |
| 300% Modulus, MPa | 3.6 | 3.2 | 3.2 | 3.5 | 5.5 | 5.9 |
| Tensile Strength, MPa | 21.8 | 26.9 | 21.4 | 26.2 | 23.6 | 23.9 |
| B. Air-Aged-48 Hours @ 212° F. ASTM D865 | | | | | | |
| Elongation, % | 270 | 330 | 400 | 400 | 450 | 460 |
| % Change | −53% | −51% | −53% | −38% | −15% | −13% |
| 300% Modulus, MPa | — | 7.9 | 6.5 | 10.5 | 5.2 | 5.4 |
| % Change | — | +147% | +103% | +200% | −5% | −8% |
| Tensile Strength, MPa | 3.4 | 8.4 | 11.4 | 18.6 | 14.5 | 16.1 |
| % Change | −84% | −69% | −47% | −29% | −38% | −33% |
| C. Air-Aged-96 Hours @ 212° F. ASTM D865 | | | | | | |
| Elongation, % | 180 | 140 | 200 | 330 | 450 | 340 |
| % Change | −68% | −79% | −67% | −49% | −15% | −36% |

| | Test Data | | | | | |
|---|---|---|---|---|---|---|
| | Blank | Agerite Stalite S | Agerite Superlite | Agerite Resin D | Example 5A | Example 6A |
| 300% Modulus, MPa | — | — | — | 8.3 | 4.4 | 4.7 |
| % Change | — | — | — | +137% | −20% | −20% |
| Tensile Strength, MPa | 2.2 | 2.5 | 3.0 | 9.1 | 9.7 | 5.8 |
| % Change | −90% | −91% | −86% | −65% | −59% | −76% |

The above results clearly demonstrate the effective antioxidant properties of the compounds of the invention in protecting natural rubber vulcanizates against heat aging deterioration.

The antioxidant compounds of the invention are also non-staining and non-discoloring, which is a very useful and important property. A disadvantage of many of the more effective antioxidants is staining and discoloration—i.e., a darkening in color of the vulcanized rubber in which they are used. This effect is particularly noticeable upon exposure to light. Articles originally of one color may take on various shades according to the amount of exposure. Staining is masked in blank articles, so the most potent antioxidants may be used, even though they are of the staining type. In many cases, for example in rubber flooring, light colors with good aging properties are essential. To meet such requirements non-staining and non-discoloring antioxidants have been developed. Until recently these were of low efficiency and only relative non-staining. Within the last few years however, intensive research by manufacturers of antioxidants has led to the introduction of new types, which combine efficiency and the absence of staining. The following tests illustrate the non-staining and non-discoloring characteristics of the products of this invention.

Contact and Migration Staining
ASTM-D925-Methods A and B on white acrylic enamel, 48 hours at 140° F. Specimens exposed 10 inches from R. S. bulb.

| Exposure Time (Hours) | Blank | Example 5A | Example 6A | Agerite Resin D |
|---|---|---|---|---|
| Staining after 24 hrs. | No migration | No migration | No migration | No migration |
| Staining after 48 hrs. | No migration No contact | No migration No contact | No migration No contact | Some migration No contact. |

I claim:

1. A compound of the formula

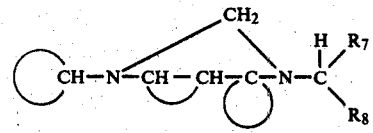

where $R_7$ is alkyl and $R_8$ is hydrogen or alkyl and where ⌣ together with the carbon or carbon atoms to which it is shown attached indicates a cyclopentyl or cyclohexyl cycloalkyl ring or such a cycloalkyl ring substituted by alkyl, halo, alkoxy or phenyl.

2. A compound of claim 1 where $R_8$ is hydrogen and $R_7$ is

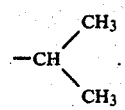

3. A compound of claim 1 of the formula

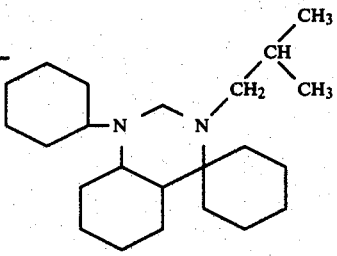

4. The compound of claim 1 where each cycloalkyl ring is a cyclohexyl ring or a cyclohexyl ring substituted by at most two alkyl groups, and the alkyl groups in the compound contain from 1 to 25 carbons.

* * * * *